United States Patent
Molaee et al.

(10) Patent No.: US 11,546,700 B2
(45) Date of Patent: Jan. 3, 2023

(54) COCHLEAR IMPLANT SYSTEM WITH AN IMPROVED SELECTION OF TEMPORAL FEATURES FOR WHICH TO BE CODED INTO STIMULATION PULSES

(71) Applicant: Oticon Medical A/S, Smørum (DK)

(72) Inventors: Behnam Molaee, Vallauris (FR); Bradford Backus, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 17/401,597

(22) Filed: Aug. 13, 2021

(65) Prior Publication Data
US 2022/0053273 A1 Feb. 17, 2022

(30) Foreign Application Priority Data
Aug. 14, 2020 (EP) ..................................... 20191127

(51) Int. Cl.
*H04R 25/00* (2006.01)
*A61N 1/36* (2006.01)
(Continued)

(52) U.S. Cl.
CPC ........... *H04R 25/505* (2013.01); *A61N 1/025* (2013.01); *A61N 1/0541* (2013.01); *A61N 1/08* (2013.01);
(Continued)

(58) Field of Classification Search
CPC ........ A61N 1/025; A61N 1/0541; A61N 1/08; A61N 1/36038; H04R 25/505; H04R 25/606
See application file for complete search history.

(56) References Cited

U.S. PATENT DOCUMENTS

| | | | |
|---|---|---|---|
| 10,166,388 B2 * | 1/2019 | Isik | A61N 1/36038 |
| 2006/0212095 A1 | 9/2006 | Wolfe et al. | |
| 2010/0198300 A1 * | 8/2010 | Smith | A61N 1/36038 |
| | | | 607/57 |

FOREIGN PATENT DOCUMENTS

| | | |
|---|---|---|
| EP | 3 061 491 A1 | 8/2016 |
| WO | WO 2017/011196 A1 | 1/2017 |
| WO | WO 2018/106567 A1 | 6/2018 |

* cited by examiner

*Primary Examiner* — Brian Ensey
(74) *Attorney, Agent, or Firm* — Birch, Stewart, Kolasch & Birch, LLP

(57) ABSTRACT

The aspect of the disclosure is achieved by a cochlear implant system which comprises a microphone unit configured to receive an acoustical signal and transmit an audio signal based on the acoustical signal and an electrode array comprising a plurality of electrodes. Furthermore, the system comprises a processor unit including a filter bank which includes multiple bandpass channels configured to divide the audio signal into multiple bandpass audio signals. Each of the multiple bandpass channel may be confined to an electrode of the plurality of electrodes. Furthermore, the system may comprise a first temporal feature extractor configured to determine a primary group of temporal features of a bandpass audio signal of the multiple bandpass audio signals, and a second temporal feature extractor configured to window filter the bandpass audio signal and determine a secondary group of temporal features of the window filtered bandpass audio signal. The system further comprises a stimulation generator configured to determine a final group of temporal features based on the primary group of temporal features and the secondary group of temporal features, and a similarity measure value of the primary and the secondary group of temporal features is determined for the final group of temporal features. The processor unit is configured to decide based on the similarity measure value whether the final (Continued)

group of temporal features is to be encoded into a stimulation pulse or to prioritize based on the similarity measure value a stimulation pulse encoded based on the final group of temporal features, and wherein the encoded stimulation pulse is transferred to an electrode of the plurality of electrodes, and where the electrode is configured to apply an electrical stimulation to a group of auditory nerve fibers of a recipient of the cochlear implant system based on the encoded stimulation pulse.

20 Claims, 11 Drawing Sheets

(51) Int. Cl.
    *A61N 1/02*           (2006.01)
    *A61N 1/05*           (2006.01)
    *A61N 1/08*           (2006.01)

(52) U.S. Cl.
    CPC ....... *A61N 1/36038* (2017.08); *H04R 25/606* (2013.01)

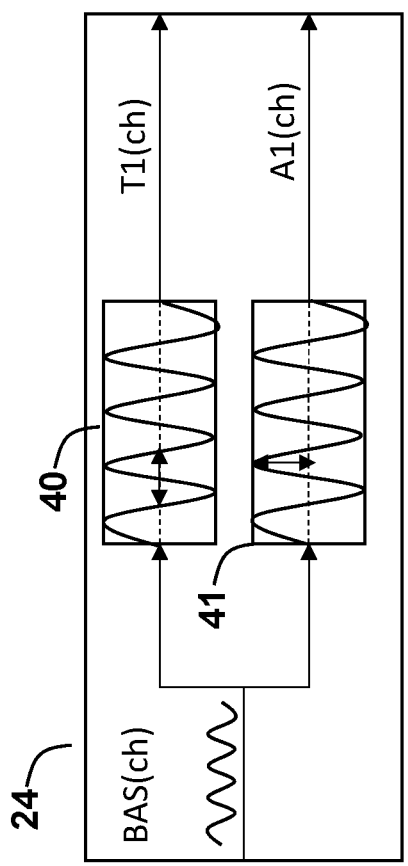
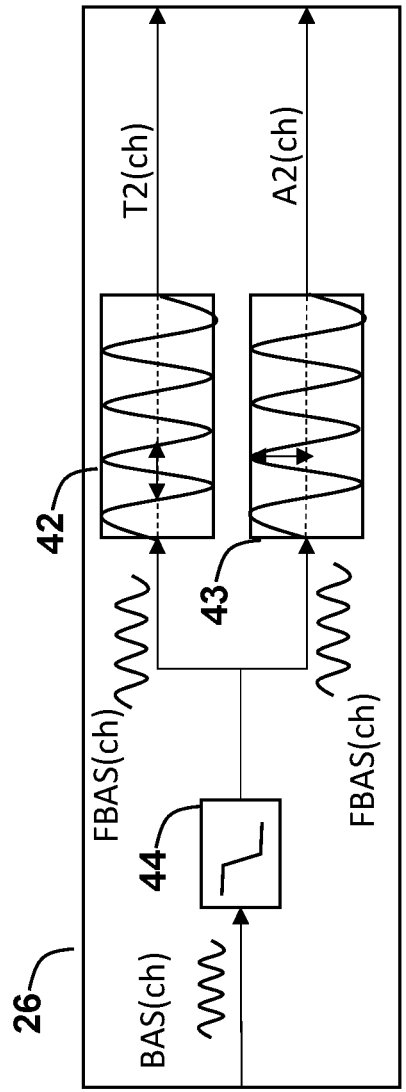
FIG. 3A
FIG. 3B

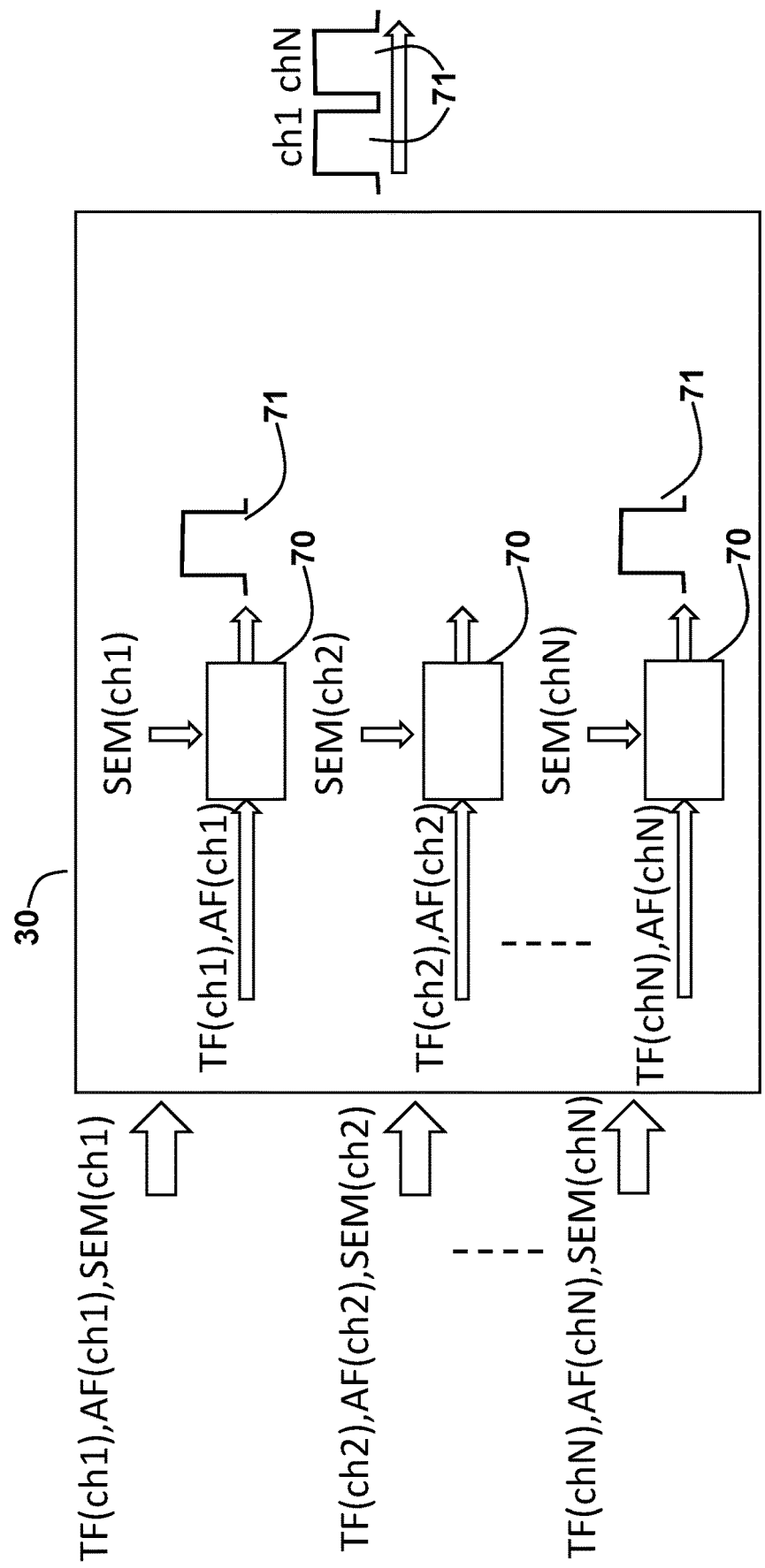

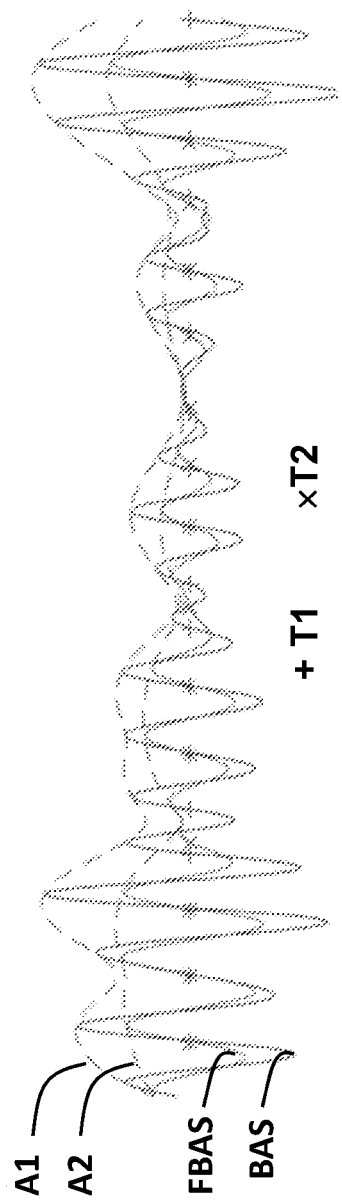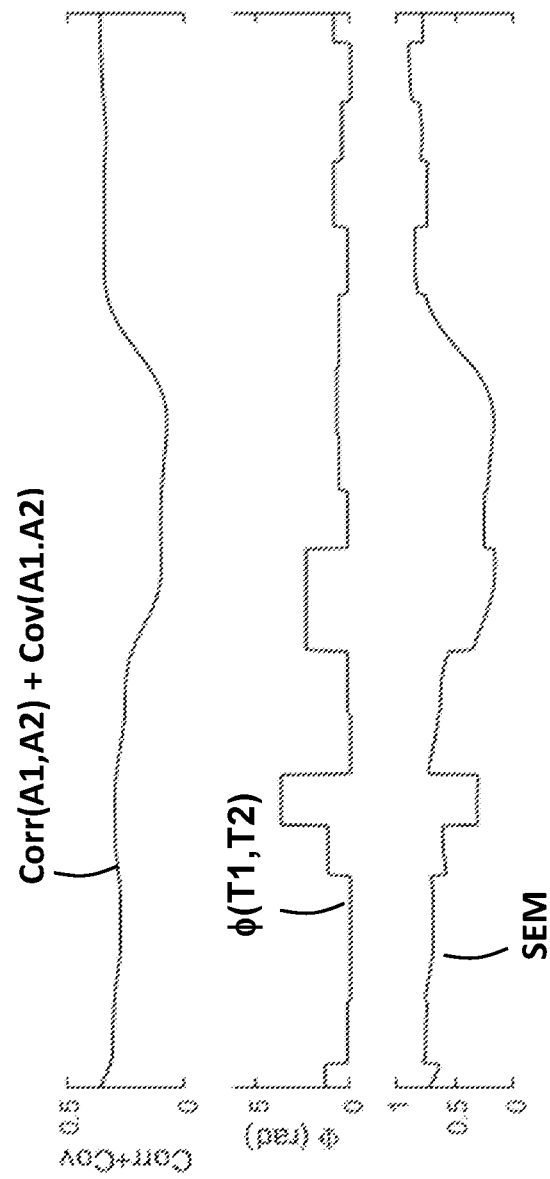
FIG. 8A  FIG. 8B  FIG. 8C  FIG. 8D

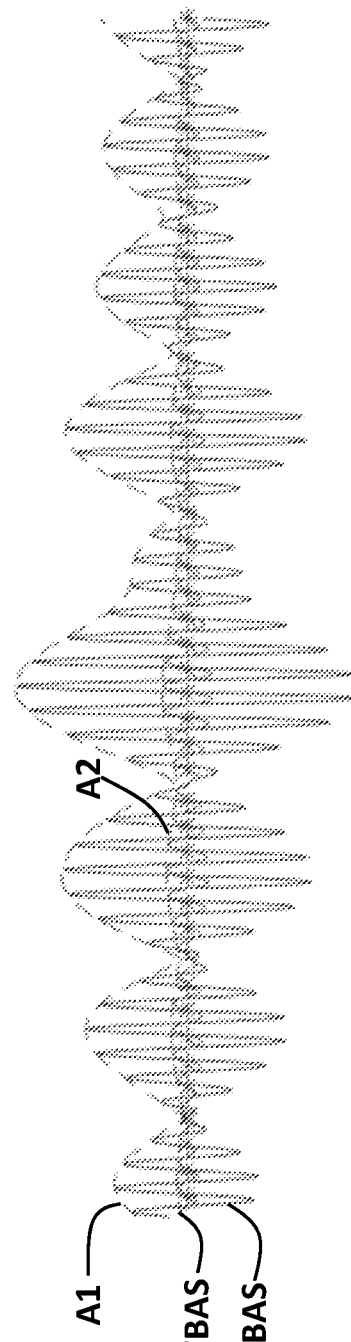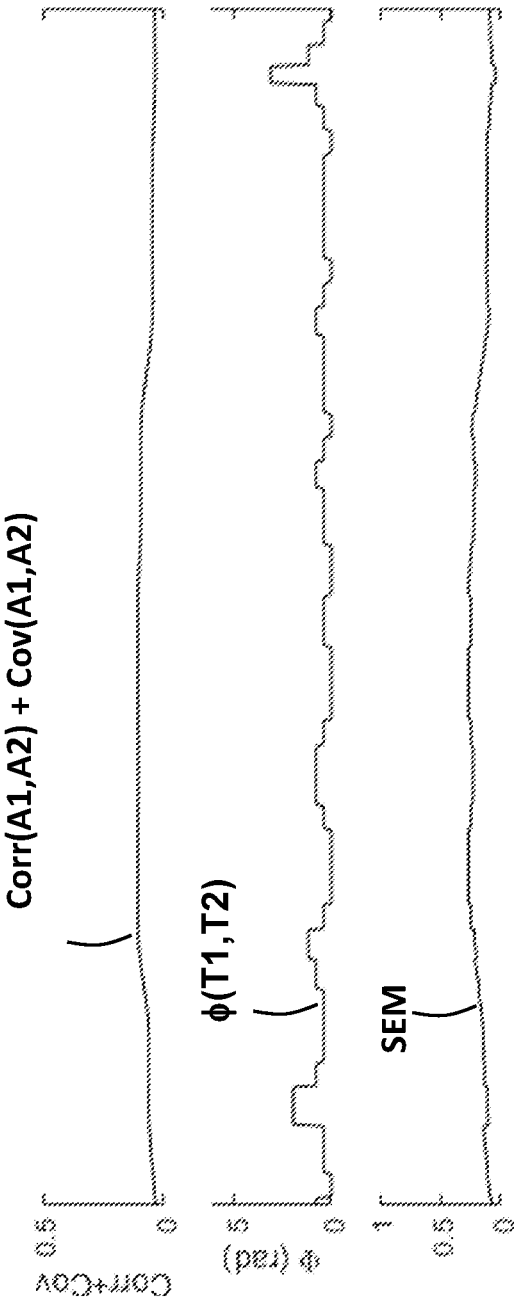

COCHLEAR IMPLANT SYSTEM WITH AN IMPROVED SELECTION OF TEMPORAL FEATURES FOR WHICH TO BE CODED INTO STIMULATION PULSES

FIELD

The present disclosure relates to a cochlear implant system. More particularly, the disclosure relates to a processor unit which is configured to decide whether a group of temporal features is to be coded into a stimulation pulse.

BACKGROUND

Known multichannel cochlear implant systems encode environmental sounds directly into a plurality of stimulation pulses which is then frame coded into one or more stimulation frames using specific temporal feature coding strategies, such as Temporal Fine Structure. Temporal Fine Structure (TFS) coding strategy considers many aspects of a normal hearing physiology. The key point in this type of coding strategy (which distinguishes it from other strategies) is that timing of electrode pulses, such as their onsets, is used to convey those temporal features that would be missing in a standard fixed rate strategy. For example, an audio signal may be divided into multiple bandpass signals, where each of the bandpass signal is confined to an electrode of the cochlear implant system, and a phase of each of the bandpass signal is usually ignored in fixed rate strategies, where in TFS coding strategies an attempt to encode this phase information as electrode timings is made. To do this, each bandpass signal and its phase are often obtained using time-domain-based analyses, such as filter banks, zero-crossing and/or Hilbert methods. Including a temporal feature, such as phase, in the coding strategy without quantifying its relevance to the hearing brain is not optimal. This is because frequently trade-offs need to be made due to implant or CI user constraints, as a simple example, one cannot stimulate the same electrode at two different rates simultaneously. This issue becomes more important as stimulation pulses conflict a lot which requires the TFS strategy to select and prioritize one pulse and either deviate or delete other pulses to make room.

Therefore, there is a need to provide a solution that addresses at least some of the above-mentioned problems.

SUMMARY

An aspect of the disclosure is to provide an improved selection of temporal features to be encoded into stimulation pulses by a cochlear implant system.

A further aspect of the disclosure is to reduce the computational power of the processor unit of the cochlear implant system.

The aspect of the disclosure is achieved by a cochlear implant system which comprises a microphone unit configured to receive an acoustical signal and transmit an audio signal based on the acoustical signal and an electrode array comprising a plurality of electrodes. Furthermore, the system comprises a processor unit including a filter bank which includes multiple bandpass channels configured to divide the audio signal into multiple bandpass audio signals. Each of the multiple bandpass channel may be confined to an electrode of the plurality of electrodes. Furthermore, the system may comprise a first temporal feature extractor configured to determine a primary group of temporal features of a bandpass audio signal of the multiple bandpass audio signals, and a second temporal feature extractor configured to window filter the bandpass audio signal and determine a secondary group of temporal features of the window filtered bandpass audio signal.

The window filter is provided for generating an envelope like output signal where temporal features that are more robust to the filtering are passing through the window filter, and thereby, the window filtered bandpass audio signal differs from the none filtered bandpass audio signal by including less temporal features.

The window filter may include a lowpass filter or a bandpass filter configured to filter the bandpass audio signal. The window filtered bandpass audio signal may include an oscillating envelope which mainly includes the fundamental frequency as the harmonic frequencies are highly attenuated because of the filtering. The cut-off frequencies(y) of the window filter may be adapted to the center frequency of a bandpass channel which provides the bandpass audio signal to be filtered by the window filter. The bandpass channel is part of the multiple bandpass channels.

The window filter may include any linear or nonlinear filter function.

For example, the higher the bandpass channel number is the higher the center frequency is, and thereby, the higher the cut-off frequencies(y) are(is).

Thereby, the cut-off frequency of the window filter may be determined by the processor unit based on a center frequency of a bandpass channel of the multiple bandpass channels which provides the bandpass audio signal.

The cut off frequency of the window filter may be determined by the processor unit based on a feedback from the second amplitude envelope detector. The feedback may include information on whether the window filtered bandpass audio signal includes an envelope for which an amplitude is able to be determined from.

The similarity measure value of the primary and the secondary group of temporal features may be determined by a cost function between the primary group of temporal features and the secondary group of temporal features.

The similarity measure value of the primary and the secondary group of temporal features may be determined by a cost function between a first primary temporal feature of the primary group of temporal features and a second primary temporal feature of the secondary group of temporal features, wherein the first primary temporal feature and the second primary temporal feature are the same type.

The first primary and second primary temporal feature are of the same type, for example onset event time or amplitude, and a first secondary of the primary group of temporal features and the second secondary temporal feature of the secondary group of temporal features are of the same type, for example onset event time or amplitude.

If the similarity of the first primary temporal feature and the second primary temporal feature is increasing the cost function decreases, and thereby, the similarity measure value increases.

The similarity measure value of the primary and the secondary group of temporal features may be determined by determining a similarity measurement between the first amplitude and the second amplitude and determining a time difference measure between the first onset event time and the second onset event time, and then, the similarity measure value may be determined by a cost function including the similarity measurement between amplitudes and the time difference measure between time onset event times.

Thereby, the similarity measure value defines a total level of similarity of both the onset event times and the amplitudes of the primary and the secondary group of temporal features.

The similarity measurement may include determining a cross-correlation between the first amplitude and the second amplitude, determining a cross-covariance between the first amplitude and the second amplitude, and then, the similarity measurement may be determined by a linear combination of the cross correlation and the cross-covariance. The linear combination may be a summation or a multiplication of the cross correlation and the cross-covariance.

Additionally, the processor unit includes a stimulation generator configured to determine a final group of temporal features based on the primary group of temporal features and the secondary group of temporal features, and furthermore, the stimulation generator may be configured to determine a similarity measure value between the primary and the secondary group of temporal features for the final group of temporal features. The processor unit may be configured to decide based on the similarity measure value whether the final group of temporal features is to be encoded into a stimulation pulse or to prioritize based on the similarity measure value a stimulation pulse encoded based on the final group of temporal features.

The encoded stimulation pulse may then be transferred to an electrode of the plurality of electrodes, and where the electrode may be configured to apply an electrical stimulation to a group of auditory nerve fibers of a recipient of the cochlear implant system based on the encoded stimulation pulse.

The processor unit may be configured to determine a final group of temporal features for each of the multiple bandpass audio signals, and a similarity measure value for each of the final group of temporal features. Furthermore, the processor unit is configured to decide based on the similarity value whether the final group of temporal features is to be encoded into a stimulation pulse, and wherein each of the encoded plurality of stimulation pulse may be transferred to a group of electrodes of the plurality of electrodes.

The primary group of temporal features may include a first onset event time of a primary event detected in a primary sequence of events of the bandpass audio signal and a first amplitude of the primary event at the first onset event time, and wherein the secondary group of temporal features may include a second onset event time of a secondary event detected in a secondary sequence of events of the window filtered bandpass audio signal and a second amplitude of the secondary event at the second onset event time. The final group of temporal features may include a final onset event time and a final amplitude, where the final onset event time may be determined based on the first onset event time and the second onset event time, and the final amplitude may be determined based on the first amplitude and the second amplitude.

The final onset event time defines the timing of the encoding of temporal features into stimulation pulses. The final onset event time may define the timing of the adaptation of power needed for transferring the encoded stimulation pulses to the auditory nerve fibers.

The final amplitude defines an amplitude level and/or a pulsewidth of the encoding stimulation pulse.

The first temporal feature extractor may comprise a first event detector configured to determine the first onset event time of the bandpass audio signal of the multiple bandpass audio signals, and a first envelope detector configured to determine the first amplitude of the bandpass audio signal of the multiple bandpass audio signals at the first onset event time, and wherein the second temporal feature extractor may comprises a second event detector configured to determine the second onset event time of the window filtered bandpass audio signal of the multiple bandpass audio signals, and a second envelope detector configured to determine the second amplitude of the window filtered bandpass audio signal of the multiple bandpass audio signals at the second onset event time.

The event detectors may be configured to determine a phase signal in time based on the bandpass audio signal (or the window filtered bandpass audio signal), where in the phase signal an onset event time is determined.

The envelope detector may be configured to determine an amplitude envelope in time based on the bandpass audio signal (or the window filtered bandpass audio signal, where in the amplitude envelope the amplitude is determined at a time equal to the onset event time.

The event detector may be configured to is configured to create a sequence of events of a bandpass audio signal of the multiple bandpass audio signals based on detecting when a phase of the bandpass audio signal exceeds a phase threshold, and where each event of the sequence of events is created based on detecting when a phase of the bandpass audio signal exceeds a phase threshold, and wherein the phase threshold may be any value between 0 and $2\pi$.

When a difference between a first primary temporal feature of the primary group of temporal features and a second primary temporal feature of the secondary group of temporal feature is below an onset event time feature threshold level or an amplitude feature threshold level, a final temporal feature of the final group of temporal features may be determined by a first weighting of the first primary temporal feature of the primary group of temporal features and a second weighting of the first secondary temporal feature of the secondary group of temporal, where the first weighting decreases while the second weighting increases and vice versa, and the sum of the first weighting and the second weighting is always 1.

When a difference between a first primary temporal feature of the primary group of temporal features and a second primary temporal feature of the secondary group of temporal feature is above an onset event time feature threshold level or an amplitude feature threshold level, a final temporal feature of the final group of temporal features may be equal to the first primary temporal feature of the primary group of temporal features.

The final temporal feature of the final group of temporal features may be determined by following equation:

$$FF(ch) \propto \begin{cases} (1 - W(F_c(ch), BW(ch))) * F1(ch) + & \text{if } |F2(ch) - F1(ch)| < \\ \quad W(F_c(ch), BW(ch)) * F2(ch) & \text{TFHR or AFHR} \\ F1(ch) & \text{Otherwise} \end{cases}$$

where $1-W(Fc(ch), BW(ch))$ is the first weighting factor which is depending on a center frequency $(Fc(ch))$ and/or a bandwidth of the bandpass channel ch of the multiple bandpass channels, and $W(Fc(ch), BW(ch))$ is the second weighting factor, $F1(ch)$ is the first primary temporal feature, (e.g. a first onset event time, $T1(ch)$, or the first amplitude $A1(ch)$), $F2(ch)$ is the second primary temporal feature, (e.g. the second onset event time, $T2(ch)$, or the second amplitude, $A2(ch)$), and TFHR is an onset event time feature threshold level and AFHR is an amplitude feature threshold level. The AFHR may vary between 0 or above. The above equation is a generalized equation for the final temporal and the final amplitude feature, but the value of the weighting factors are not the same between the final temporal feature (TF) and the final amplitude feature (AF).

The second weighting factor increases in relation to a decrease of the center frequency, and the second weighting factor decreases in relation to an increase of the center frequency.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 3A and 3B illustrate an example of a temporal feature extractor;

FIGS. 7A and 7B illustrate another example of the processor unit;

FIGS. 8A to 8D illustrate a graphical example of a similarity value; and

FIGS. 9A to 9D illustrate another graphical example of a similarity value.

DETAILED DESCRIPTION

Figure 1:
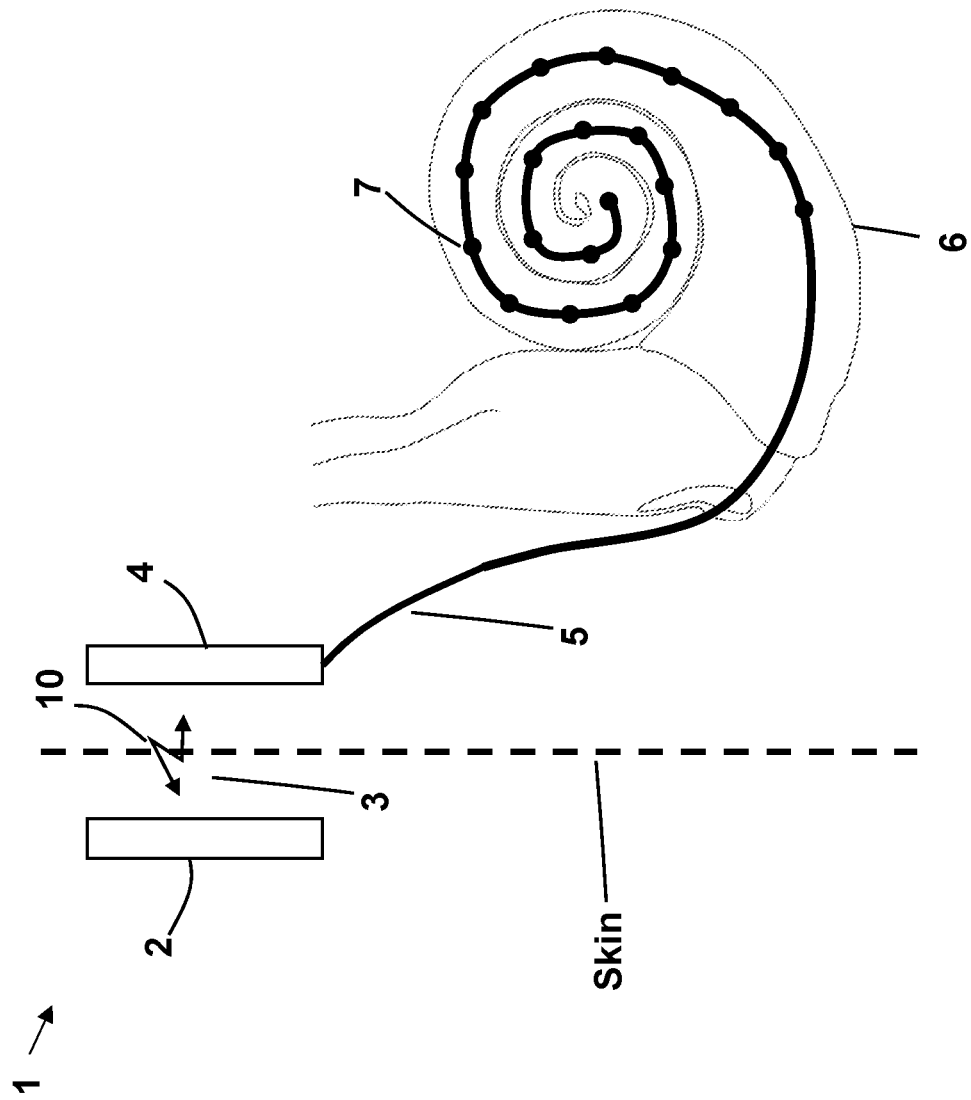
FIG. 1 illustrates an example of a cochlear implant system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing aid may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing aidhearing aid" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing aidhearing aid is adapted to be worn in any known way. This may include i) arranging a unit of the hearing aidhearing aid behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing aidhearing aid entirely or partly in the pinna and/or in the ear canal of the user such as in an In-the-Ear type hearing aid or In-the-Canal/Completely-in-Canal type hearing aid, or iii) arranging a unit of the hearing aidhearing aid attached to a fixture implanted into the skull bone such as in a Bone Anchored Hearing Aid or a Cochlear Implant, or iv) arranging a unit of the hearing aidhearing aid as an entirely or partly implanted unit such as in a Bone Anchored Hearing Aid or a Cochlear implant system. The hearing aidhearing aid may be implemented in one single unit (housing) or in a number of units individually connected to each other.

A "hearing system" refers to a system comprising one or two hearing aidhearing aids, and a "binaural hearing system" refers to a system comprising two hearing aidhearing aids where the devices are adapted to cooperatively provide audible signals to both of the user's ears. The hearing system or binaural hearing system may further include one or more auxiliary device(s) that communicates with at least one hearing aidhearing aid, the auxiliary device affecting the operation of the hearing aidhearing aids and/or benefitting from the functioning of the hearing aidhearing aids. A wired or wireless communication link between the at least one hearing aid and the auxiliary device is established that allows for exchanging information (e.g. control and status signals, possibly audio signals) between the at least one hearing aid and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing aid. The remote control is adapted to control functionality and/or operation of the at least one hearing aid. The function of the remote control may be implemented in a smartphone or other (e.g. portable) electronic device, the smartphone/electronic device possibly running an application (APP) that controls functionality of the at least one hearing aid.

In general, a hearing aid includes i) a receiving unit such as a microphone for receiving an acoustic signal from a user's surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The receiving unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing aids, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing aid comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

Now referring to FIG. 1, which illustrates a cochlear implant system 1 which includes an external unit 2 and an implantable unit 4 which are able to communicate transcutaneoulsy 3 through the skin of the user of the system 1. The implantable unit 4 is connected to an electrode array 5 which is configured to be inserted into the cochlea 6 of the user. The electrode array may include a plurality of electrodes 7.

Figure 2:
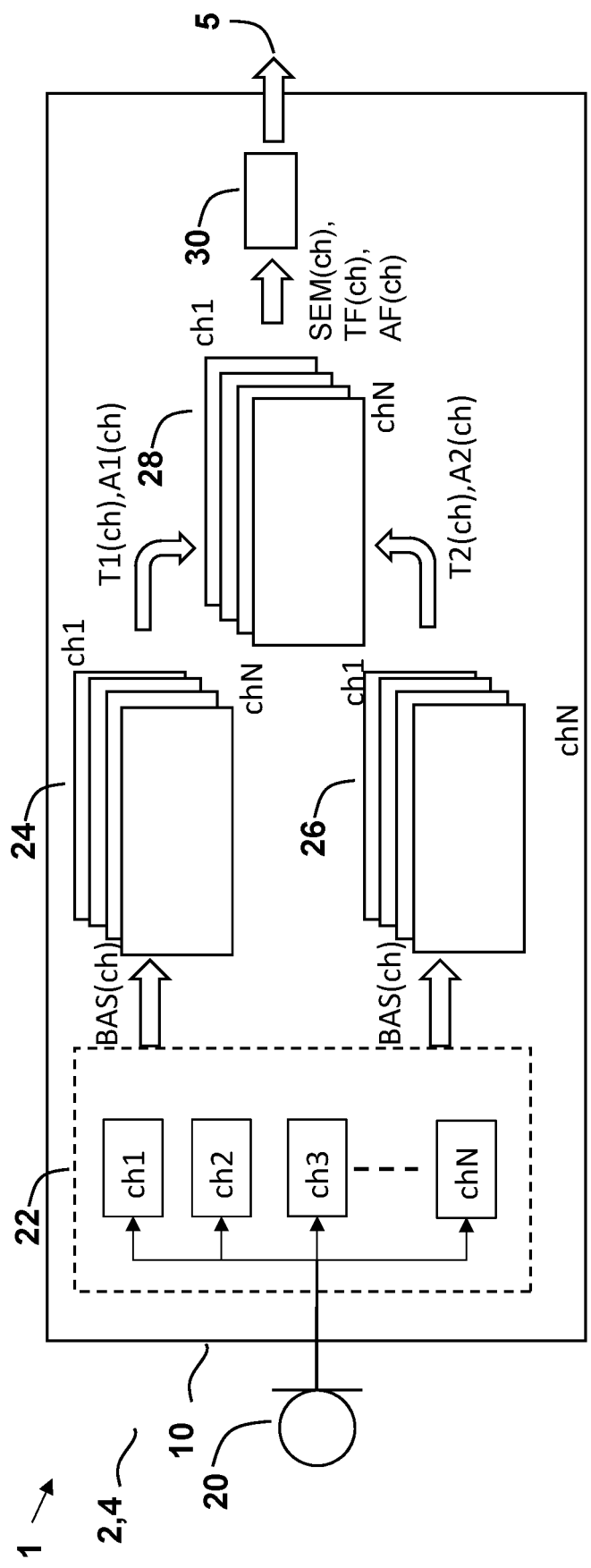
FIG. 2 illustrates another example of the cochlear implant system.

FIG. 2 illustrates the cochlear implant system 1 comprising a microphone unit 20 configured to receive an acoustical signal and transmit an audio signal based on the acoustical signal. The system 1 comprises a processor unit 10 which includes a filter bank 22 configured to receive the audio signal. The filter bank 22 includes multiple bandpass channels (ch1–chN) configured to divide the audio signal into multiple bandpass audio signals BAS, and each of the multiple bandpass audio BAS(ch) is transmitted to a first temporal feature extractor 24 and a second temporal feature extractor 26 of the processor unit 10. The first temporal feature extractor is configured to determine a primary group of temporal features of a bandpass audio signal of the multiple bandpass audio signals, and the second temporal feature extractor is configured to window filter the bandpass audio signal and determine a secondary group of temporal features of the window filtered bandpass audio signal. In this specific example, the primary group of temporal features includes a first onset event time T1(ch) and a first amplitude A1(ch) of the primary event at the first onset event time T1(ch) of a primary event, and in this specific example, the secondary group of temporal features includes a second onset event time T2(ch) of a secondary event and a second amplitude A2(ch) of the secondary event at the second onset event time.

Both groups of temporal features (A1(ch),T1(ch),A2(ch), T2(ch)) are transmitted to a stimulation generator 28 which is configured to determine a final group of temporal features (AF(ch), TF(ch)) based on the primary group of temporal features (A1(ch),T1(ch)) and the secondary group of temporal features (A2(ch),T2(ch)). The stimulation generator determines for the final group of temporal features (AF(ch), TF(ch)) a similarity measure value (SEM(ch)) based on the primary and the secondary group of temporal features In this specific example, the final group of temporal features includes a final onset event time TF(ch) and a final amplitude AF(ch), where the final onset event time TF(ch) is determined based on the first onset event time T1(ch) and the second onset event time T2(ch), and the final amplitude AF(ch) is determined based on the first amplitude A1(ch) and the second amplitude A(ch).

The processor unit 10 is then configured to decide 30 based on the similarity measure value (SEM(ch)) whether the final group of temporal features (AF(ch), TF(ch)) is to be encoded into a stimulation pulse or to prioritize 30 based on the similarity measure value (SEM(ch)) a stimulation pulse encoded based on the final group of temporal features (AF(ch), TF(ch)), and wherein the encoded stimulation pulse is transferred to an electrode 7 of the electrode array 5, and where the electrode 7 is configured to apply an electrical stimulation to a group of auditory nerve fibers of a recipient of the cochlear implant system based on the encoded stimulation pulse 61.

FIGS. 3A and 3B illustrate an example of a temporal feature extractor (24, 26). Both examples of a temporal feature extractor comprises an event detector and an envelope detector, where the event detector is configured to create a sequence of events of a bandpass audio signal of the multiple bandpass audio signals based on detecting when a phase of the bandpass audio signal exceeds a phase threshold, and where each event of the sequence of events is created based on detecting when a phase of the bandpass audio signal exceeds a phase threshold, and where each event of the sequence of events is created based on detecting when a phase of the bandpass audio signal exceeds a phase threshold, and wherein the phase threshold may be any value between 0 and 2n. The envelope detector is configured to determine an amplitude of the bandpass audio signal of the multiple bandpass audio signals at a given time an event is detected, i.e. at an event onset time. FIG. 3A illustrates an example of the first temporal feature extractor 24 which is configured to receive the bandpass audio signal BAS(ch) from a bandpass channel ch, and the bandpass audio signal is divided into two parts, where the first part is received by a first event detector 40 configured to determine the first onset event time T1(ch) when a phase in the bandpass audio signal exceeds the phase threshold. The second part is received by a first envelope detector 41 configured to determine the first amplitude A1(ch) of the bandpass audio signal at the first onset event time T1(ch).

The first event detector 40 may be configured to determine a phase signal in time based on the bandpass audio signal, where in the phase signal the first onset event time T1(ch) is determined.

The first envelope detector 41 may be configured to determine an amplitude envelope in time based on the bandpass audio signal, where in the amplitude envelope the first amplitude A1(ch) is determined at a time equal to the first onset event time T1(ch).

FIG. 3B illustrates an example of the second temporal feature extractor 24 which is configured to receive the bandpass audio signal BAS(ch) from a bandpass channel ch, and the bandpass audio signal is passing through a window filter 44 before divided into two parts, where the first part is received by a second event detector 42 configured to determine the second onset event time T2(ch) when a phase in the window filtered bandpass audio signal FBAS(ch) exceeds the phase threshold. The second part is received by a second envelope detector 43 configured to determine the second amplitude A2(ch) of the window filtered bandpass audio signal FBAS(ch) at the second onset event time T2(ch).

The second event detector 42 may be configured to determine a phase signal in time based on the window filtered bandpass audio signal, where in the phase signal the second onset event time T2(ch) is determined.

The second envelope detector 43 may be configured to determine an amplitude envelope in time based on the window filtered bandpass audio signal, where in the amplitude envelope the second amplitude A2(ch) is determined at a time equal to the second onset event time T2(ch).

Figure 4A:
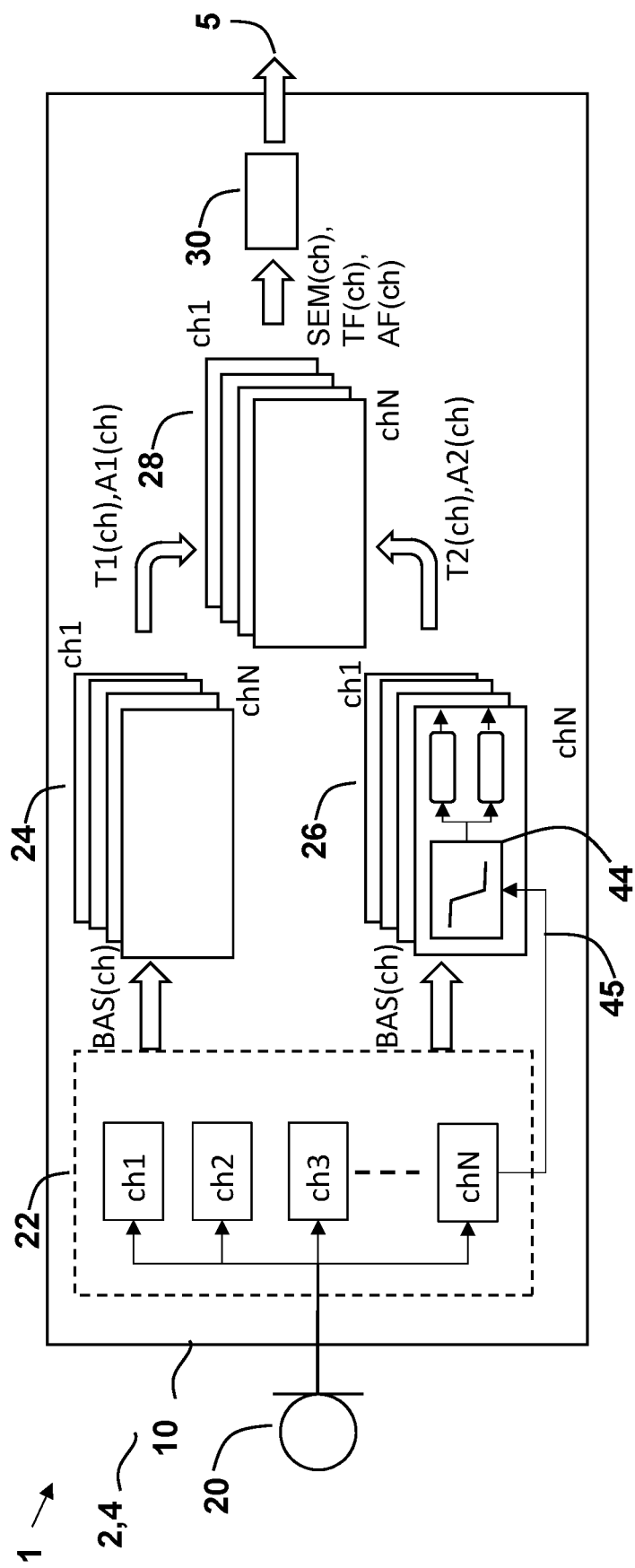
FIGS. 4A and 4B illustrate an example of the window filter.
Figure 4B:
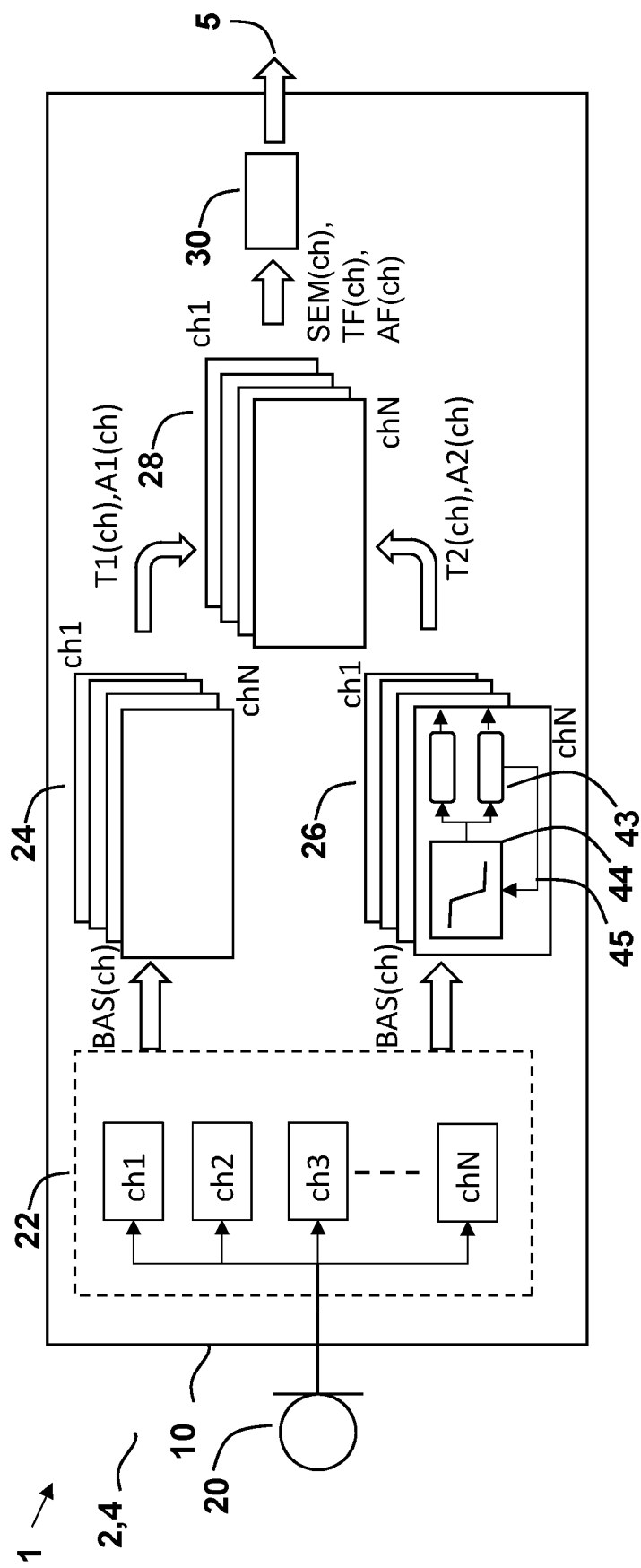

FIGS. 4A and 4B illustrate an example of how cut-off frequencies(y) of the window filter 44 is determined by the processor unit 10. In FIG. 4A, the processor unit 10 is configured to adapt the cut-off frequencies(y) of the window filter based on a center frequency 45 and/or a bandwidth 45 of a bandpass channel ch which provides the bandpass audio signal BAS(ch) to be filtered by the window filter 44. The window filter 44 may be a bandpass filter, and the processor unit 10 is configured to determine the cut-off frequencies of the bandpass filter 44 based on a center frequency 45 and/or a bandwidth 45 of the bandpass channel ch which provides the bandpass audio signal BAS(ch) to be filtered by the window filter 44. If the window filter 44 is a lowpass filter, the processor unit 10 is configured to determine a cut-off frequency of the lowpass filter 44 based on the center frequency 45 and/or the bandwidth 45 of the bandpass channel ch. For example, if the center frequency of the bandpass channel is 1000 Hz and the bandwidth is 200 Hz, the cut-off frequency of a lowpass filter 44 may be set to about 1100 Hz, or the cut-off frequencies of a bandpass filter 44 is set to about 900 Hz and about 1100 Hz.

In FIG. 4B, the processor unit 10 is configured to adapt the cut-off frequencies(y) of the window filter 44 based on a feedback 45 from the second amplitude envelope detector 43. The feedback includes information on whether the window filtered bandpass audio signal FBAS(ch) includes an envelope for which an amplitude is able to be determined from. If the feedback 45 includes information on that an amplitude is not able to be determined, the processor unit 10 adapts the cut-off frequencies(y) of the window filter 44 until an amplitude can be determined.

Figure 5:
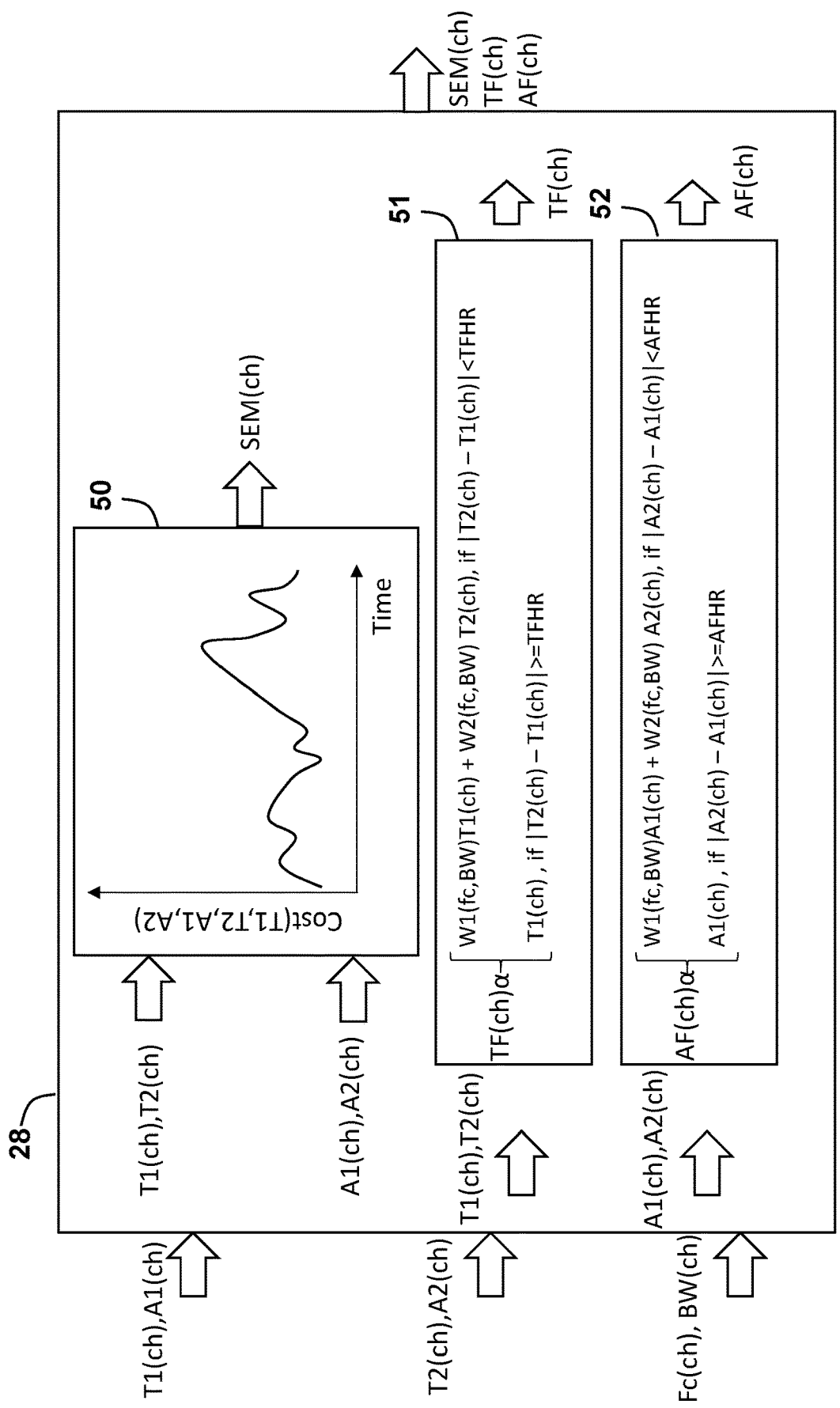
FIG. 5 illustrates an example of the stimulation generator.

FIG. 5 illustrates an example of the stimulation generator 28 configured to determine 50 the similarity measure value SEM(ch) based on a cost function between the primary group of temporal features (T1(ch),A1(ch)) and the secondary group of temporal features (T2(ch),A2(ch)).

The similarity measure value (SEM) of the primary and the secondary group of temporal features may be determined by a cost function between a first primary temporal feature (e.g. T1) of the primary group of temporal features and a second primary temporal feature (e.g. T2) of the secondary group of temporal features.

The similarity measure value (SEM) of the primary and the secondary group of temporal features may be determined by a cost function between a first secondary temporal feature (e.g. A1) of the primary group of temporal features and a second secondary temporal feature (e.g. A2) of the secondary group of temporal features.

A final temporal feature (TF, AF) of the final group of temporal features is determined in 51 and 52 by a weighting function when a difference between a first primary temporal feature of the primary group of temporal features and a second primary temporal feature of the secondary group of temporal feature is below an onset event time feature threshold level (TFHR) or an amplitude feature threshold level(AFHR), where TFHR and AFHR are not the same. The weighting function includes a first weighting of the first primary temporal feature of the primary group of temporal features and a second weighting of the first secondary temporal feature (e.g. T2) of the secondary group of temporal, where the first weighting decreases while the second weighting increases, and vice versa, and the sum of the first weighting and the second weighting is always 1. If the difference is equal or above the temporal or amplitude feature threshold the final temporal feature is equal to the first primary temporal feature of the primary group of temporal features. More specifically, in 51, when a difference between the first onset event time T1(ch) and the second onset event time T2(ch) is below the temporal features threshold level (TFHR), the final onset event time TF(ch) is determined by the weighting function which includes a first weighting of the first onset event time and a second weighting second onset event time, where the sum of the first weighting and the second weighting is always 1. In 51, when the difference between the first onset event time T1(ch) and the second onset event time T2(ch) is equal or above the onset event time feature threshold (TFHR), the final onset event time TF(ch) is equal to the first onset event time T1(ch).

In 52, when a difference between the first amplitude A1(ch) and the second amplitude A2(ch) is below the amplitude features threshold level (AFHR), the final amplitude AF(ch) is determined by the weighting function which includes a first weighting of the first amplitude and a second weighting of the second amplitude, where the sum of the first weighting and the second weighting is always 1. In 52 when the difference between the first amplitude A1(ch) and the second amplitude A2(ch) is equal or above the amplitude temporal feature threshold (AFHR), the final amplitude AF(ch) is equal to the first amplitude A1(ch).

Figure 6A:
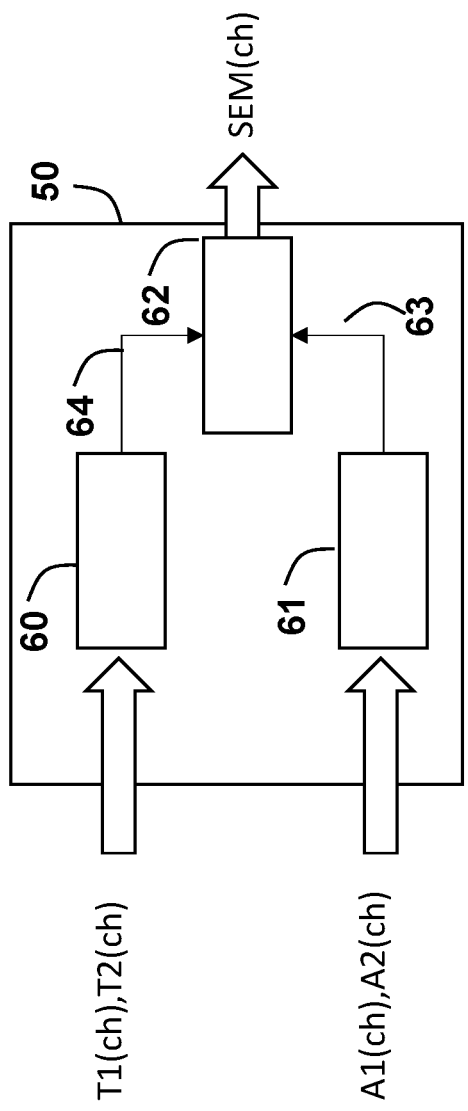
FIGS. 6A and 6B illustrate an example of the processor unit.
Figure 6B:
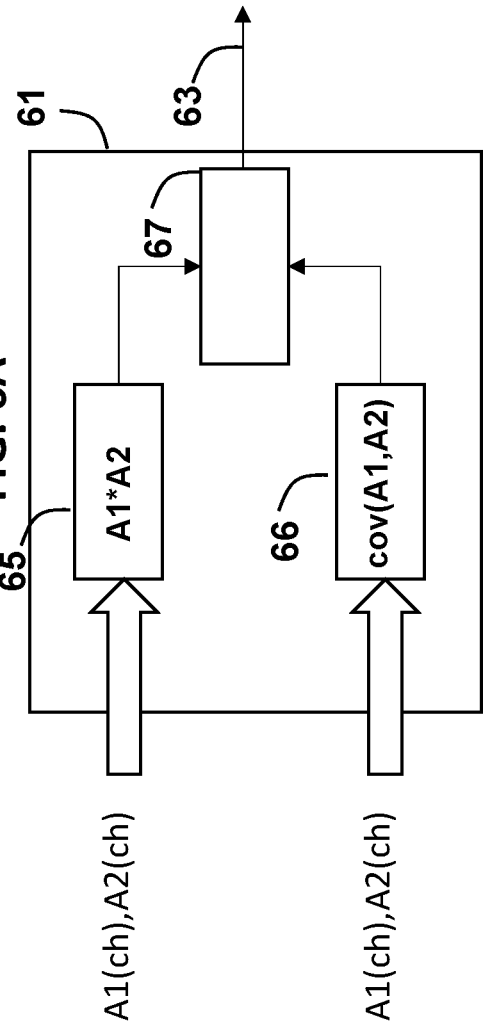

FIGS. 6A and 6B illustrate a more specific example of how the processor unit 10 determines 50 the similarity measure value SEM(ch). In FIG. 6A, the similarity measure value of the primary and the secondary group of temporal features may be determined by determining a similarity measurement 61 between the first amplitude A1(ch) and the second amplitude A2(ch) and determining a time difference measure 60 between the first onset event time T1(ch) and the second onset event timeT2(ch), and then, the similarity measure value SEM(ch) is determined by a cost function 62 including an output 64 from the similarity measurement 60 and an output 63 from the time difference measure 63. In FIG. 6B, the similarity measurement 61 may include determining a cross-correlation 65 between the first amplitude A1(ch) and the second amplitude A2(ch), determining a cross-covariance 66 between the first amplitude A1(ch) and the second amplitude A2(ch), and then, the similarity measurement 61 may be determined by a linear combination 67 of the cross correlation 65 and the cross-covariance 66. The linear combination 67 may be a summation or a multiplication of the cross correlation 65 and the cross-covariance 66.

Figure 7B:
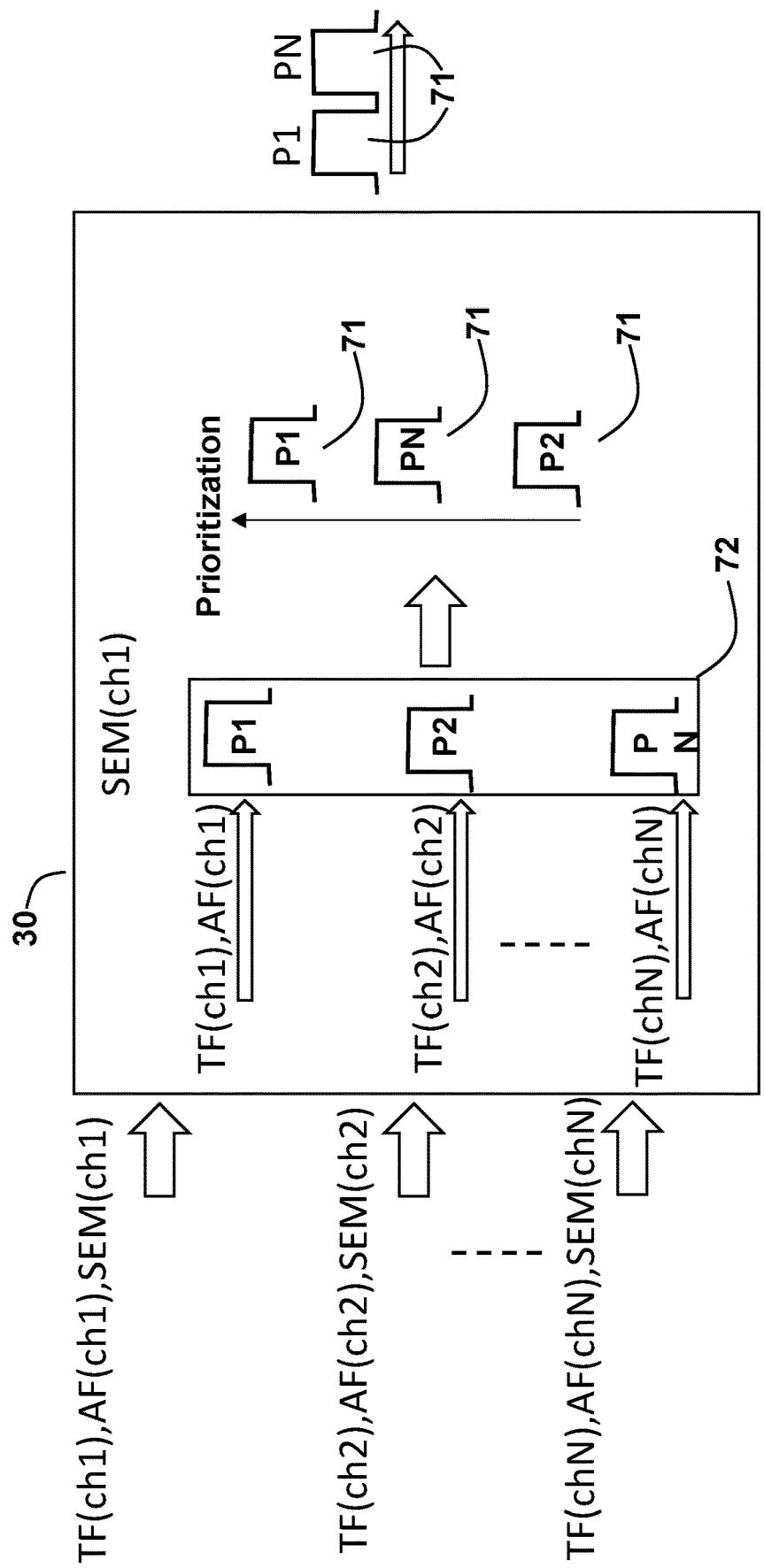

FIGS. 7A and 7B illustrate an example of the processor unit 10 configured to decide 30 based on the similarity measure value (SEM(ch)) whether the final group of temporal features (AF(ch), TF(ch)) is to be encoded into a stimulation pulse or to prioritize 30 based on the similarity measure value (SEM(ch)) a stimulation pulse encoded based on the final group of temporal features (AF(ch), TF(ch)). FIG. 7A illustrates an example where the processing unit 10 has decided (30, 70) that the final group of temporal features of the bandpass channel ch1 and chN are to be encoded into stimulation pulses 71 and transmitted to the electrode array 5. FIG. 7B illustrates an example where the processor unit 10 encodes the multiple final groups of temporal features of multiple bandpass channels (ch1,ch2, and chN) into multiple stimulation pulses (P1, P2, PN) and prioritize (30, 72) each of the multiple stimulation pulses. In this example, the stimulation pulse P2 and PN are to be activated at the same time determined by the final onset event times TF(ch2) and TF(chN), respectively. That creates a timing conflict between P2 and PN, and since the prioritization of PN is higher than P2, stimulation pulse P2 is discarded and not transmitted to the electrode array 5. In another example, stimulation pulse P2 would be delayed a bit so that no timing conflict will appear between P2 and PN.

FIGS. 8A to 8D illustrate a graphical example on variation in the similarity measure value with respect to time for a low frequency bandpass audio signal. The time frame for each graph in FIGS. 8A to 8D are aligned. FIG. 8A illustrates an envelope of the bandpass audio signal BAS and an envelope of the window filtered bandpass audio signal FBAS. Furthermore, the figure illustrates a variation of the first amplitude A1 and the second amplitude A2 along the envelope of the bandpass audio signal BAS and the window filtered bandpass audio signal FBAS, respectively. Additionally, the first onset event time T1 and the second onset event time T2 are illustrated on the same curve. FIG. 8B illustrates a graph of the similarity measurement of the first amplitude A1 and the second amplitude A2, where in this example, the similarity measurement includes a combination of cross-correlation and cross-covariance of the first and the second amplitude. FIG. 8C illustrates a graph of the time difference measurement 4 between the first onset event time and the second onset event time. FIG. 8D illustrates a graph which includes variation of the similarity measure value SEM in relation to variations in the amplitudes (A1, A2) and the onset event time (T1, T2). It is seen that when the time difference measurement increases φ the similarity measure value SEM decreases and if the similarity measurement cross+cov decreases the similarity measure value SEM decreases.

FIGS. 9A to 9D illustrate a similar example as illustrated in FIGS. 8A to 8D where the bandpass audio signal corresponds to a higher frequency range.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant system comprising,
   a microphone unit configured to receive an acoustical signal and transmit an audio signal based on the acoustical signal,
   an electrode array comprising a plurality of electrodes,
   a processor unit including;
      a filter bank including multiple bandpass channels configured to divide the audio signal into multiple bandpass audio signals,
      a first temporal feature extractor configured to determine a primary group of temporal features of a bandpass audio signal of the multiple bandpass audio signals,
      a second temporal feature extractor configured to window filter the bandpass audio signal and determine a secondary group of temporal features of the window filtered bandpass audio signal of the multiple bandpass audio signals,
      a stimulation generator configured to determine a final group of temporal features based on the primary group of temporal features and the secondary group of temporal features, and a similarity measure value of the primary and the secondary group of temporal features is determined for the final group of temporal features, and
   wherein the processor unit is configured to decide based on the similarity measure value whether the final group of temporal features is to be encoded into a stimulation pulse or to prioritize based on the similarity measure value a stimulation pulse encoded based on the final group of temporal features, and wherein the encoded stimulation pulse is transferred to an electrode of the plurality of electrodes, and where the electrode is configured to apply an electrical stimulation to a group of auditory nerve fibers of a recipient oaf the cochlear implant system based on the encoded stimulation pulse.

2. A cochlear implant system according to claim 1, wherein the processor unit is configured to determine a final group of temporal features for each of the multiple bandpass audio signals, and a similarity measure value for each of the final group of temporal features, and decide for each of the final group of temporal features based on the similarity value whether it is to be encoded into a stimulation pulse, and wherein each of the encoded plurality of stimulation pulse is transferred to a group of electrodes of the plurality of electrodes.

3. A cochlear implants stem according to claim 1, wherein the primary group of temporal features includes a first onset event time of a primary event detected in a primary sequence of events of the bandpass audio signal and a first amplitude of the primary event at the first onset event time, and wherein the secondary group of temporal features includes a second onset event time of a secondary event detected in a secondary sequence of events of the window filtered bandpass audio signal and a second amplitude of the secondary event at the second onset event time, and wherein the final group of temporal features includes a final onset event time and a final amplitude, where the final onset event time determined based on the first onset event time and the second onset event time, and the final amplitude is determined based on the first amplitude and the second amplitude.

4. A cochlear implant system according to claim 3, wherein the first temporal feature extractor comprises;
a first event detector configured to determine the first onset event time of the bandpass audio signal of the multiple bandpass audio signals, and
a first envelope detector configured to determine the first amplitude of the bandpass audio signal of the multiple bandpass audio signals at the first onset event time, and
wherein the second temporal feature extractor comprises,
a second event detector configured to determine the second onset event time of the window filtered bandpass audio signal of the multiple bandpass audio signals, and
a second envelope detector configured to determine the second amplitude of the window filtered bandpass audio signal of the multiple bandpass audio signals at the second onset event time.

5. A cochlear implant system according to claim 1, wherein the window filter includes a lowpass filter or a bandpass bite e filter the bandpass audio signal.

6. A cochlear system according to claim 1, wherein the window filtered bandpass audio signal includes an oscillating envelope.

7. A cochlear implant system according o claim 6, wherein a cutoff frequency of the window filter is determined by the processor unit such that an oscillating envelope appears in the window filtered bandpass audio signal.

8. A cochlear in plant system according to claim 7, wherein the cutoff frequency of the window filter is determined by the processor unit based on a center frequency and/or bandwidth of a bandpass channel of the multiple bandpass channels which provides the bandpass audio signal.

9. A cochlear implant system according to claim 1, wherein the similarity measure value of the primary and the secondary group of temporal features is determined by a cost function between the primary group of temporal features and the secondary group of temporal features.

10. A cochlear implant system according to claim 3, wherein the similarity measure value of the primary and the secondary group of temporal features is determined by:
determining a similarity measurement between the first amplitude and the second amplitude,
determining a time difference measure between the first onset event time and the second onset event time, and
wherein the similarity measure value is determined by a cost function including the similarity measurement and the time difference measure.

11. A cochlear implant system according to claim 10, wherein the similarity measurement includes:
determining a cross-correlation between the first amplitude and the second amplitude,
determining a cross-covariance between the first amplitude and the second amplitude, and
wherein the measurement is determined by a linear combination of the cross correlation and the cross-covariance.

12. A cochlear implant system according to claim 2, wherein the first temporal feature is the first onset event time and the second temporal feature is the second onset event time.

13. A cochlear implant system according to claim 1, wherein the similarity measure value of the primary and the secondary group of temporal features is determined by a real-value function between a first temporal feature of the primary group of temporal features and a second temporal feature of the secondary group of temporal features.

14. A cochlear implant system according to claim 2, wherein the first temporal feature is the first amplitude and the second temporal feature is the second amplitude.

15. A cochlear implant system according to claim 1, wherein the final group of temporal features is determined based on a function including a first weighting of the primary group of temporal features and a second weighting of the secondary group of temporal features, and wherein the first weighting and the second weighting are determined based on a center frequency and/or a bandwidth of a bandpass channel of the multiple bandpass channels respective to the bandpass audio signal.

16. A cochlear implant system according to claim 4, wherein an event detector, such as the first event detector and the second event detector, is configured to create a sequence of events of a bandpass audio signal of the multiple bandpass audio signals, where each event of the sequence of events is created when a phase of the bandpass audio signal exceeds a phase threshold, and wherein the phase threshold may be any value between 0 and $2\pi$.

17. A cochlear implant system according to claim 1, where a final temporal feature (FF) of the final group of temporal features relates to a first primary temporal feature (F1) of the primary group of temporal features and to a second primary temporal feature (F2) of the secondary group of temporal features in following way:

$$FF(ch) \propto \begin{cases} (1 - W(F_c(ch), BW(ch))) * F1(ch) + & \text{if } |F2(ch) - F1(ch)| < \\ W(F_c(ch), BW(ch)) * F2(ch) & TFHR \text{ or } AFHR \\ F1(ch) & \text{Otherwise} \end{cases},$$

where 1-W(Fc(ch), BW(ch)) is the first weighting factor which is depending on a center frequency (Fc(ch)) and/or a bandwidth (BW(ch)) of the handpass channel ch of the multiple bandpass channels, and W(Fc(ch), BW(ch)) is the second weighting factor, F1(ch) is the first primary temporal feature, F2(ch) is the second primary temporal feature, and TFHR is an onset event time feature threshold level and AFHR is an amplitude feature threshold level.

18. A cochlear implant system according to claim 17, where the second weighting factor increases in relation to a decrease of the center frequency, and the second weighting factor decreases in relation to an increase of the center frequency.

19. A cochlear implant system according to claim 2, wherein the primary group of temporal features includes a first onset event time of a primary event detected in a primary sequence of events of the bandpass audio signal and a first amplitude of the primary event at the first onset event time, and wherein the secondary group of temporal features includes a second onset event time of a secondary event detected in a secondary sequence of events of the window filtered bandpass audio signal and a second amplitude of the secondary event at the second onset event time, and Therein the final group of temporal features includes a final onset event time and a final amplitude, where the final onset event time is determined based on the first onset event tune and the second onset event time, and the final amplitude is determined based on the first amplitude and the second amplitude.

20. A cochlear implant system according to claim 2, wherein the window filter includes a lowpass filter or a bandpass filter configured to filter the bandpass audio signal.

* * * * *